(12) United States Patent
Flüh et al.

(10) Patent No.: US 6,324,901 B1
(45) Date of Patent: Dec. 4, 2001

(54) PROCESS AND DEVICE FOR RECOGNIZING FOREIGN BODIES IN VISCOUS OR FLUID, LUMP-CONTAINING FOODSTUFFS

(76) Inventors: Gerd Flüh, Töingstr. 21, D-21399 Lüneburg; Wolfgang Katten, Kräuterweg 26, D-51069 Köln; Josef Krieger, Peter-Engels-Str. 13, D-50354 Hürth; Manfred Rost, Böcklinstr. 75, D-50389 Wesselimg, all of (DE)

( * ) Notice: Subject to any disclaimer, the term of this patent is extended or adjusted under 35 U.S.C. 154(b) by 0 days.

(21) Appl. No.: 08/935,491
(22) PCT Filed: May 19, 1994
(86) PCT No.: PCT/EP94/01623
§ 371 Date: Mar. 11, 1996
§ 102(e) Date: Mar. 11, 1996
(87) PCT Pub. No.: WO94/27142
PCT Pub. Date: Nov. 24, 1994

Related U.S. Application Data

(63) Continuation-in-part of application No. 08/557,058, filed as application No. PCT/EP94/01623 on May 19, 1993, now abandoned.

(30) Foreign Application Priority Data

May 19, 1993 (DE) .................................................. 43 16 833
Aug. 10, 1993 (DE) .................................................. 43 26 765

(51) Int. Cl.[7] .................................................. G01N 29/02
(52) U.S. Cl. .................. 73/61.75; 73/61.79; 73/64.53; 73/598; 73/600; 73/627; 73/628
(58) Field of Search .................. 73/61.45, 61.49, 73/61.75, 61.79, 64.53, 597, 598, 599, 600, 627, 628

(56) References Cited

U.S. PATENT DOCUMENTS

| | | | |
|---|---|---|---|
| 3,608,715 | * | 9/1971 | Snyder et al. .................. 23/61.75 X |
| 4,015,470 | * | 4/1977 | Morrison .......................... 73/64.53 X |
| 4,208,915 | * | 6/1980 | Edwards ................................. 73/620 |
| 4,384,476 | * | 5/1983 | Black et al. .......................... 73/61.79 |
| 4,739,662 | * | 4/1988 | Foote ............................. 73/61.75 X |
| 5,026,564 | * | 6/1991 | Hayden ................................ 426/237 |
| 5,049,400 | * | 9/1991 | Hayden ................................ 426/237 |
| 5,181,778 | * | 1/1993 | Beller ................................ 73/597 X |

FOREIGN PATENT DOCUMENTS

| | | | |
|---|---|---|---|
| 3825131 | * | 1/1990 | (DE) . |
| 1018781 | * | 2/1966 | (GB) .................................... 73/61.79 |
| 1346095 | * | 2/1974 | (GB) . |

OTHER PUBLICATIONS

Miles et al., "Attenuation of Ultrasound in Milks and Creams", Ultrasonics, vol. 28, Nov. 1990, pp. 394–400.*

* cited by examiner

Primary Examiner—Daniel S. Larkin
(74) Attorney, Agent, or Firm—John Lezdey & Assoc

(57) ABSTRACT

A process and device are disclosed for recognizing foreign bodies in viscous or fluid masses with lumpy foodstuffs. The mass to be checked runs through a measurement section, in which, pulsed ultrasonic signals are emitted through the mass, are reflected after passing through the mass, and after passing again through the mass they are received and compared with the ultrasonic echo of the reflection surface. When the changes of the received signals exceed a predetermined threshold value, a warning or actuating signal is generated to interrupt mass advance. The parameters to be evaluated for the signal may be their amplitudes, as well as the speed of change of their amplitudes or the propagation times.

4 Claims, 2 Drawing Sheets

Fig. 1 (revised)

Figure 1:
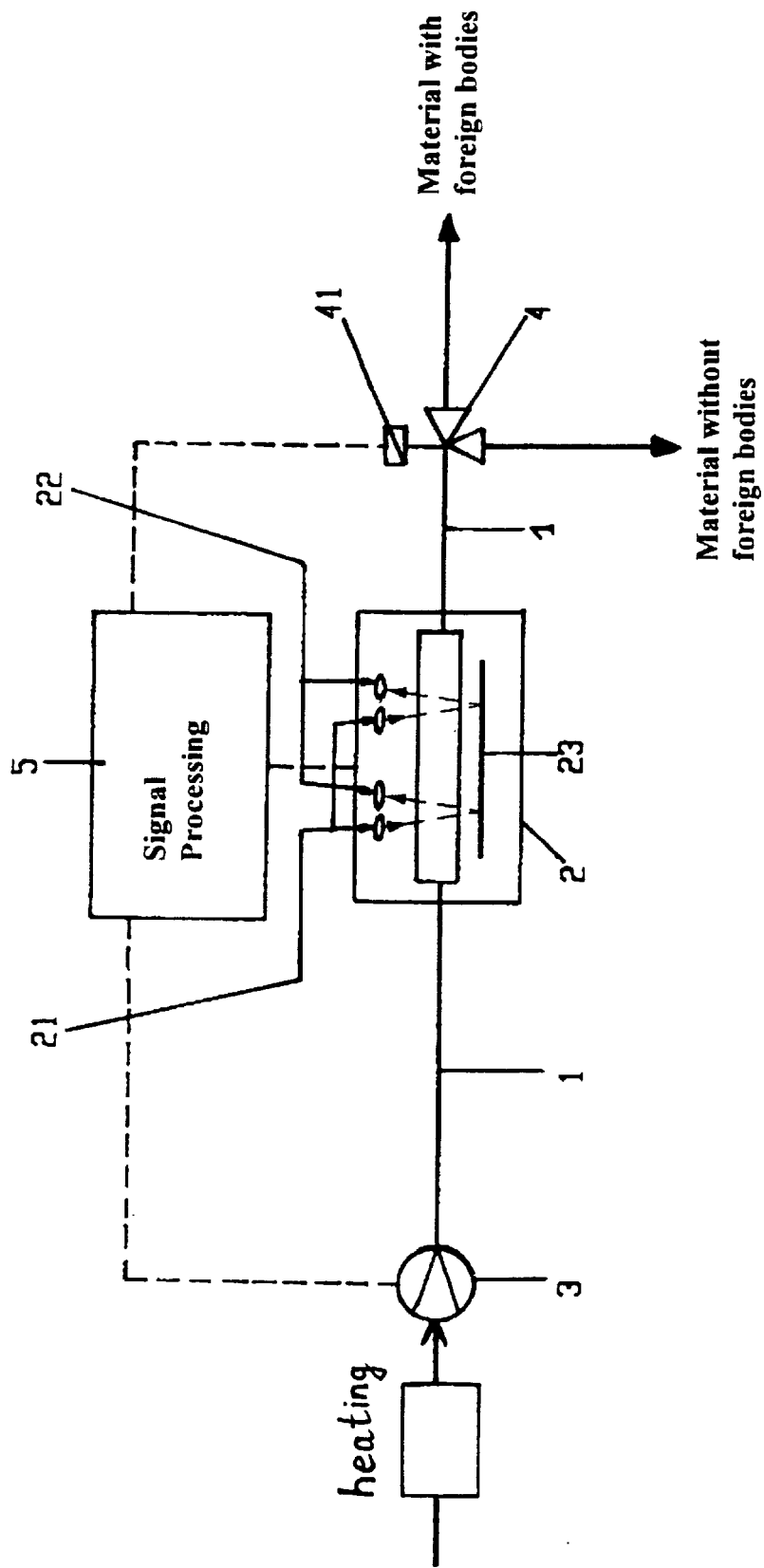

PROCESS AND DEVICE FOR RECOGNIZING FOREIGN BODIES IN VISCOUS OR FLUID, LUMP-CONTAINING FOODSTUFFS

This is a continuation-in-part of application Ser. No. 08/557,058, filed Mar. 11, 1996, now abandoned, which is a 371 of PCT/EP94/01623 filed May 19, 1993.

BACKGROUND OF THE INVENTION

1. Field of the Invention

The invention refers to a method for detecting foreign bodies in liquid or solid material masses, especially in foods, as wall as to a device for implementing this method.

2. Description of the Prior Art

Numerous foods, especially milk products, e.g. yoghourts as well as baby food, are often produced on large scale in industrial manufacturing processes. Before filling the finished foods, a thorough examination for any foreign bodies possibly existing is required among other tasks. These foreign bodies can get into the foods during the production process on the one hand, or, on the other hand, they can exist in individual ingredients, e.g. fruit.

Within fish processing, light tables are used, e.g. for examining fish fillets. For obvious reasons, however, these tables are not suitable for examining the foods mentioned above and, in addition, they have the disadvantage that the actual testing is made by visual inspection and it cannot therefore be automated.

Moreover, there are known X-ray apparatuses using X-rays according to the same principle in which the visual inspection is made via a display screen. This method has one additional disadvantage, viz. the corresponding working places are subjected to increased intensity of radiation.

From DE-OS 40 13 402, a process for the detection of gas bubbles in liquid-filled pipes is known, as well as the device needed for this process, in which a transmitter and a receiver are positioned on either side of the pipe and transmit single impulses fixed in length and level to determine the presence of gas bubbles within the pipe through the change in the impulses after traversing the liquid. This well-known process is not suitable for the examination mentioned above since it can only detect a gas phase within a liquid phase. The difference in density between gas and liquid is much higher than that between foreign bodies and food (viscose mass and liquid mass).

From the magazine "Elektronik", Nr. 25/1991, a "particle detective" is known that works with high frequency ultrasound according to the (Doppler) principle. The disadvantage of this method is that it again is very work-intensive and cannot be automated.

Finally, in U.S. Pat. No. 4,607,520, a process and a device for the detection of bubbles in a flow of liquid is described. For this process, ultrasound impulses are sent through a designated segment of the liquid to be examined. During a time frame that is opened after the impulse running time, it is checked whether the impulses reached the receiver. If this is not the case, it is assumed that there is a lack of homogency (a gas bubble) within the designated segment. Again, this process is not suitable for the testing of food for any foreign body contents.

The invention was therefore based on the requirement to specify a method for detecting foreign bodies in viscous or liquid material masses, especially in foods, as well as a device for implementing this method and also enabling automated testing.

SUMMARY OF THE INVENTION

As to the method, this requirement is met by continuous conveying of the material mass at predetermined speed through a measurement line section, by the transmission of ultrasonic signals through the material mass transported in the measurement line section, by the reception of the transmitted ultrasonic signals after passing through the material mass, by a comparison of at least one received ultrasonic signal with at least one transmitted ultrasonic signal for detecting variations of at least one predefined signal parameter, as well as by generating an alarm and/or activation signal when the variation of at least one signal parameter exceeds or falls short of a predetermined limit value, in order to interrupt the material transport and/or to divert the material mass from the transport flow.

Foreign bodies can be recognized quite easily even if the foods screened are not homogenous, but contains solid pieces, as long as the length and frequency of the ultrasound impulses transmitted are predetermined. In that case, a weakening in amplitude without a change in duration of the impulse signals the presence of a foreign body, whereas the presence of e.g. a piece of fruit or another form of concentration as well as a lowering in the concentration of sugar would cause a change in duration of the signal as well as a weakening in amplitude.

One especially advantageous development of this process is to warm up the mass to be tested before running the examination. This method leads to improved results, especially in goods containing pectine, where the foreign bodies (i.e. seeds) are much better discernable from solid pieces of food (i.e. pieces of fruit).

The process preferably also contains an adaptive reinforcement of the ultrasound signal/s and/or an adaptation of the border value/s. This allows for an optimum adaptation to the permeability and consistency of the good to be examined.

Finally, it is also possible to control the amplitudes of the sent ultrasound signals in such a way that the amplitudes of the received ultrasound signals are constant, where the change in manipulated variable is compacted to the predetermined border value. The ultrasound signals are preferably pulsed, so that the running time between transmitter and receiver provides an additional controlling value.

The device according to invention comprises at least one ultrasonic transmitter and at least one ultrasonic receiver, with the measurement line section being led through between the transmitter and the receiver. As an alternative to this, the device can also have a reflector from which the ultrasonic signals are reflected after passing through the measurement line section, pass through the measurement line again, and are finally picked up by the receiver(s). A wall of the measurement line section, e.g. a tube wall, can likewise be used for sound reflection.

One advantage of these solutions lies in the fact that the application of ultrasonic signals leads to no radiation exposure of the environment and that they can be implemented at very low cost because the transmitter and receiver elements, as well as the evaluation unit, require no costly safety provisions, and because generally available standard products can be used. Apart from this, it is quite easy to make a fail-safe test setup for ultrasonic testing due to the fact that high-frequency acoustic signals generally do not exist in the environment at all—or they only exist with very low intensity—and they can be easily screened.

In addition, the power consumption of a corresponding device according to invention is very low in comparison with the known devices or methods mentioned.

One of the predetermined signal parameters is preferably the amplitude of the ultrasonic signals.

Besides, the speed of the variation of amplitude of several ultrasonic signals received successively can also be used as an additional or alternative signal parameter.

Furthermore, a signal parameter—preferably the amplitude of the transmitted ultrasonic signal—can be controlled in such a way that the amplitude of the received signal remains constant, with the variation of the manipulated variable being compared with a predetermined limit value.

It is also possible to modulate the transmitted ultrasonic signals and to evaluate a phase displacement between the transmitted and the received signal as signal parameter.

The preferred method for detecting foreign bodies, which influence ultrasonic signals in quite different ways, is either to use several ultrasonic transmitters operating at different frequencies, or to trigger an ultrasonic transmitter so that its frequency always covers a predefined frequency band.

Several single transmitters and, if applicable, the receiver allocated to each transmitter are preferably Clocked individually in order to avoid mutual interferences.

If the material mass to be tested is filled in receptacles, with the receptacles being formed in a second material mass within the measurement line section, foods that are already packed can also be tested for foreign bodies. In this case, the second material mass serves as a transmitting medium for acoustic signals which pass through the receptacle and the foods contained therein.

The device according to invention is preferably integrated into a filling and/or packing system, in which case the device is provided with a downstream switch by means of which the transported material mass or receptacle is diverted when the activation signal is generated.

Further details, characteristics and advantages of the invention result from the following description of execution examples based on a drawing.

BRIEF DESCRIPTION OF THE PREFERRED DRAWINGS

Figure 2:
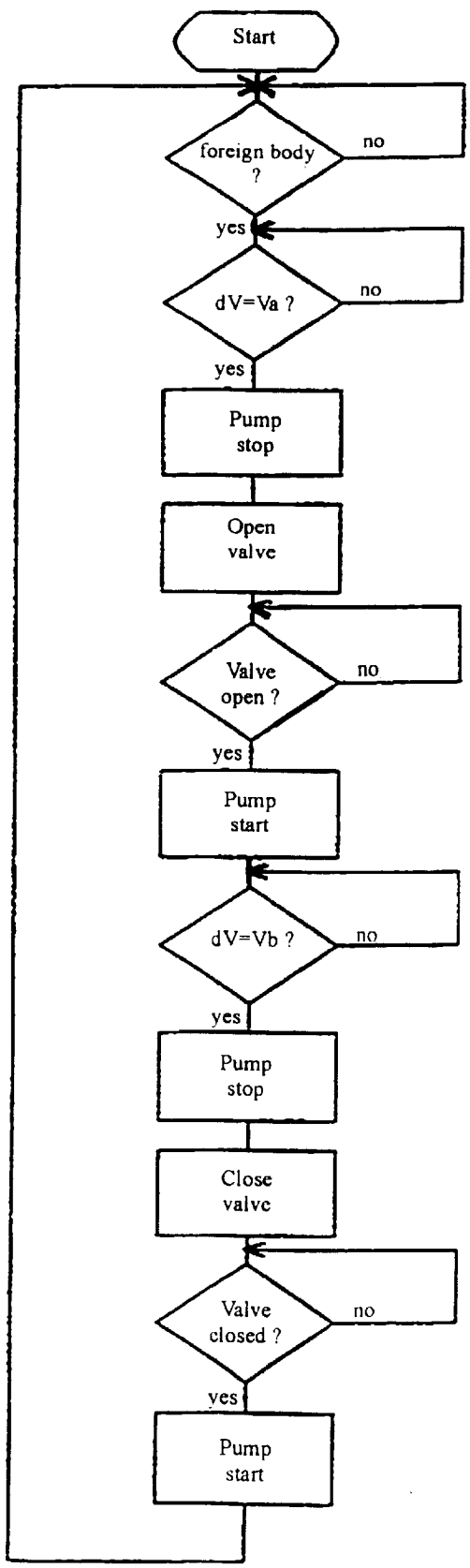

The following are shown:

FIG. 1 a block diagram of a device according to invention for implementing the method and FIG. 2 a flow diagram of the operational mode of a device for implementing the method.

DESCRIPTION OF THE PREFERRED DRAWINGS

According to FIG. 1, a conveying line 1 has been provided for the material mass (foods) to be tested. At the input end of the conveying line 1 there is a pump 3 which is triggered by a signal processing unit 5. The material mass to be tested is transported through a measurement line section 2 and, after that, it is either fed to a packing station via a valve 4 or diverted from the transport flow if foreign bodies were detected in the material mass in the measurement line section. The valve 4 is switched over with the signal processing unit 5, for example by actuating a solenoid valve 41 The data acquired in the measurement line section are processed and evaluated as usual in the signal processing unit 5.

The measurement line section 2 contains one or several pairs of ultrasonic transmitters 21 and ultrasonic receivers 22. The execution type shown here is provided with several ultrasonic transmitters 21 and several ultrasonic receivers 22, mainly placed side by side on one side of the transport flow. Arranged on the other side of the transport flow is a reflector 23 from which the signals emitted by one transmitter Z1 toward the allocated receiver 22 are reflected in each case. The corresponding transmitter-receiver pairs in each case are preferably triggered (clocked) successively in order to prevent mutual interferences. As described above, the received signals are monitored as to any variation of predetermined signal parameters. If these variations exceed a predetermined limit value, the solenoid 41 of the valve 4 is triggered, and the material mass is diverted from the conveying line until the signal parameters are again below the predetermined limit value. Depending on the length of the measurement line section of the conveying line volume between the measurement line section and the valve, and on the conveying speed, the valve 4 remains switched over beyond this point of time until the material mass tested in the measurement line section and showing signal parameters that exceed the limit values is removed from the transport flow.

The amplitude of the received signal compared with the amplitude of the transmitted signal can be easily evaluated as signal parameter. Provided there is no foreign body in the material mass, the received signal is basically free from interferences and only affected by the acoustic characteristics of the material mass. In order to be able to test material masses of differing consistency and showing different acoustic characteristics, the limit values for the deviation of the received signal from the transmitted signal are preferably adjustable. The adjustment of these values can be made automatically at the beginning of the conveying process, e.g. by adapting the limit values to the sound absorption of the material mass.

If the transported material mass contains a foreign body, either the received signal is attenuated by an increased absorbing effect or the time of flight is reduced by a premature reflection. This interference in the signal intensity or variation of the time of flight is detected and evaluated in the signal processing unit 5. Since the transmitters are preferably operated in pulsed mode, the evaluation in view of a reduction of the signal time of flight caused by a reflection from a foreign body is also possible as against the reflection from the reflector.

In one realized appliance, an ultrasound module with several channels was used, which can be used with four pairs of test devices in a transmission technique. The measurement was taken in sequential multiplex operation. Each testing channel was provided with a blind with an amplitude checking device. Reinforcement and thresholds were adapted to provide an optimal rate of recognition of foreign bodies. A microcontroller serves for control and evaluation.

The repetition frequency of the ultrasound measurement could be controlled via the control surface. The impulse following frequency amounted to a maximum of 4 kHz in total, which is equal to a rhythm of 1 kHz for four channels. The measurements took place in a frequency area of between 0.1 and 20 MHz. Within the blind, the maximum values (positive and negative half-wave) were measured. The blind was stated in between 10 $\mu$s and 30 $\mu$s and had a width in the area of 3 to 6 $\mu$s.

The evaluation was done automatically, where the reinforcement and the evaluation threshold were manually adjustable in each channel. The finish of the event was activated as soon as the threshold had been passed n times (n: any value between 1 and 256).

If the material mass to be tested shows e.g. a very irregular consistency, which results in a stronger variation of the intensity of the received signal, the speed of an amplitude variation can also be used as an additional or alternative signal parameter, especially when comparing ultrasonic signals received successively.

An especially large measuring range is obtained if the amplitudes of the transmitted ultrasonic signals are continuously readjusted so that the amplitude of the received signals remains constant, with the manipulated variable now being evaluated as a signal parameter.

As the transmitted ultrasonic signals pass through the measurement line section twice in the execution type shown here, an increased sensitivity is achieved as opposed to the alternative in which the transmitters and receivers are positioned on the one or the other side of the measurement line section.

FIG. 2 shows a flow diagram of the operational mode of a device for detecting and separating foreign bodies from a conveyed material mass. The primary task is to find out if there is a foreign body or not. As soon as a foreign body is detected, a test is carried out to find out whether the conveyed material volume dV following the foreign body detection is equal to a volume of the conveying line between the measurement line section and valve (clearance volume Va). If this condition is met and the material mass containing the foreign body has reached the valve, the pump operation is stopped and the valve is opened. As soon as the valve is open, the pump is again switched on and operated until the conveyed material volume dV is equal to the discharge volume Vb. If this condition is met, the pump is again stopped and the valve Is switched back to its original position. After reaching this switching position, the pump is again put into operation until a new foreign body is detected. The volumes Va and Vb can be preset in an appropriate manner in this connection.

The device according to invention can be easily combined with a system for mixing, filling and/or packing of homogeneous and inhomogeneous foods.

The principle according to invention is also suitable for detecting foreign bodies, e.g. bones or fish bones in meat or fish, i.e. mainly in solid masses.

LIST OF REFERENCE MARKS 1 conveying line
2 measurement line section
3 pump
4 valve
5 signal processing unit
21 ultrasonic transmitter
22 ultrasonic receiver
23 reflector
41 solenoid valve

We claim:

1. A method of detecting the same or different foreign bodies in viscous or liquid foodstuff masses in receptacles in which said foodstuff masses contain lumpy particles by the reflection or absorption of sound, the method comprising the steps of:

(a) conveying the foodstuff mass at a predefined speed through a measurement line section;

(b) transmitting at least one ultrasonic signal having a predetermined amplitude through the foodstuff mass as the foodstuff mass passes through the measurement line section, said receptacles acting as a transmitting medium for acoustic signals;

(c) receiving the transmitted ultrasonic signal after it passes through the foodstuff mass and any changes in the transmitted signal caused by reflection or absorption by a foreign body;

(d) comparing at least one received ultrasonic signal with at least one transmitted ultrasonic signal;

(e) detecting variations of at least one predetermined signal parameter between the received transmitted and reflected ultrasonic signal and the transmitted ultrasonic signal;

(f) generating an activation signal when the variation in the pre-determined signal parameter exceeds or falls below a predetermined limit value; and (g) interrupting or diverting the transportation of the foodstuff mass when the activation signal is generated.

2. The method according to claim 1, wherein the predetermined signal parameter is the amplitude of the ultrasonic signals.

3. The method according to claim 1, wherein the predetermined signal parameter is the speed of the amplitude variations of several of the ultrasonic signals received successively.

4. The method according to claim 1, wherein the predetermined signal parameter is the time of the flight of the ultrasonic signals between an ultrasonic transmitter and an ultrasonic receiver.

* * * * *